United States Patent [19]
Pudleiner et al.

[11] Patent Number: 6,150,489
[45] Date of Patent: Nov. 21, 2000

[54] THERMOPLASTIC POLYURETHANES CONTAINING ACTIVE SUBSTANCES

[75] Inventors: Heinz Pudleiner, Krefeld, Germany; Ralf Dujardin, Novi, Mich.; Hartwin Hobler, Wuppertal, Germany

[73] Assignee: Bayer Aktiengesellschaft, Leverkusen, Germany

[21] Appl. No.: 09/254,831

[22] PCT Filed: Sep. 8, 1997

[86] PCT No.: PCT/EP97/04868

§ 371 Date: Mar. 12, 1999

§ 102(e) Date: Mar. 12, 1999

[87] PCT Pub. No.: WO98/11860

PCT Pub. Date: Mar. 26, 1998

[30] Foreign Application Priority Data

Sep. 20, 1996 [DE] Germany .................. 196 38 570

[51] Int. Cl.[7] .................................................. C08G 18/30
[52] U.S. Cl. .............................. 528/49; 528/72; 528/73; 524/718; 424/78.08; 424/78.3
[58] Field of Search ................. 528/73, 49, 72; 524/718; 424/78.08, 78.3

[56] References Cited

U.S. PATENT DOCUMENTS

| | | | |
|---|---|---|---|
| 4,925,668 | 5/1990 | Khan et al. | 424/422 |
| 4,973,320 | 11/1990 | Brenner | 604/265 |
| 5,432,185 | 7/1995 | Behner et al. | 514/356 |
| 5,503,844 | 4/1996 | Kwiatek et al. | 424/449 |
| 5,798,115 | 8/1998 | Santerre et al. | 424/423 |

FOREIGN PATENT DOCUMENTS

| | | |
|---|---|---|
| 0659442 | 6/1995 | European Pat. Off. . |
| 550875 | 4/1998 | European Pat. Off. . |
| 2901774 | 7/1980 | Germany . |
| 4221665 | 8/1993 | Germany . |

OTHER PUBLICATIONS

Munchner Medizinische Wachenschrift, 130 (Month unavailable) 1988, pp. 809–814, K. Schror, "Azetylsalizylsaure—von Antirheumatikum zum Antithrombotikum".

Justus Liebings Annanlen der Chemie, 562, pp. 75–136, Dec. 11, 1948, Von Werner Siefken, "Mono– und Polyisocyanate, IV. Mitteilung uber Polyurethane".

*Primary Examiner*—Rachel Gorr
*Attorney, Agent, or Firm*—Joseph C. Gil; Aron Preis

[57] ABSTRACT

This invention relates to thermoplastic polyurethanes (TPUs) which contain pharmaceutical active ingredients in a homogeneous distribution, to a method of producing them, and to their use in medical articles. During the production of the TPUs, compounds having an antithrombotic or antibacterial effect are added to the monomer mixture.

9 Claims, No Drawings

THERMOPLASTIC POLYURETHANES CONTAINING ACTIVE SUBSTANCES

This invention relates to thermoplastic polyurethanes (TPUs) which contain pharmaceutical active ingredients in a homogeneous distribution, to a method of producing them, and to their use in medical articles. During the production of the TPUs, compounds having an antithrombotic or antibacterial effect are added to the monomer mixture.

In addition to suitable mechanical properties and good biocompatibility or good compatibility with blood, Materials which are used in medicine and which come into direct contact with blood, e.g. artificial organs, artificial blood vessels, catheters, blood transfusion devices, also have to exhibit an antithrombotic and/or antibacterial effect.

Polymer materials are known for medical applications which comprise coatings which contain heparin or another substance having an antithrombotic effect. However, since only small amounts of active ingredient can be incorporated in the applied coating, a sufficiently high concentration of the active ingredient is not available on the surface of the medical article over the entire duration of use thereof.

Methods of incorporating substances having an antithrombotic effect in the outer polymer layer of medical articles are also known. According to EP-A 550 875, medical articles made of polymeric material are pretreated with a solvent so that a pharmaceutically active layer can penetrate the polymer. This method is costly on an industrial scale and employs organic solvents which for the most part cannot be removed from the material without leaving a residue. Moreover, only a low surface concentration of the substance is obtained.

The antithrombotic effect of acetylsalicylic acid is known (Münchner Medizinische Wochenschrift 130 (1988) 809). According to DE-C 42 21 665, esters or mixed esters of acetylsalicylic acid are added to polymers as additives in order to suppress the clotting of blood. However, it has proved to be a disadvantage in that only special derivatives of acetylsalicylic acid can be used, and the surfaces do not achieve their optimum biocompatibility until some time has elapsed, since the active ingredient first has to migrate to the surface of the polymer.

According EP-A 659 442, a mixture of amide wax and acetylic acid ethylenediamine is added to the granulated polymer material, to speed up this process of migration, before thermoplastic processing is effected. The amide wax melts during processing and, due to its incompatibility with the polymer, migrates to the surface of the finished part. The migration of the acetylsalicylic acid derivative is thereby assisted. However, only limited amounts of active ingredient can be added to the granular material and can thereby be incorporated in the medical article. Moreover, a special derivative of acetylsalicylic acid is also required for this method.

A common feature of all the aforementioned methods is that providing articles for medical use with a pharmacologically active substance necessitates an additional operation, namely either the pretreatment of the polymer material before processing or subsequent treatment of the mouldings produced. This gives rise to additional costs and is accompanied by an increase in the time which is required for production. It has now been found that, for the production of articles for medical use from thermoplastic polyurethanes, active ingredients can be added even during the production of the polymer. The polymer which is obtained can be further processed, in a conventional manner and without additional cost, to produce articles for medical use which contain active ingredients.

The present invention therefore relates to a method of producing thermoplastically processable polyurethanes which contain active ingredients by the reaction of the polyurethane-forming components A) an organic diisocyanate, B) a linear hydroxyl-terminated polyol with a molecular weight of 500 to 10,000, C) chain extenders with a molecular weight of 60 to 500, and D) 0.01 to 10% by weight, with respect to the total amount of starting materials, of a pharmacologically active substance, wherein the molar ratio of the NCO groups in A) to the groups in B) and C) which are reactive towards isocyanate is 0.9 to 1.2.

Examples of organic diisocyanates A) include aliphatic, cycloaliphatic, araliphatic, heterocyclic and aromatic diisocyanates such as those which are described in Justus Liebigs Annalen der Chemie 562, pages 75–136. Aliphatic and cycloaliphatic diisocyanates are preferred.

The following examples should be cited in particular: aliphatic diisocyanates such as hexamethylene diisocyanate, cycloaliphatic diisocyanates such as isophorone diisocyanate, 1,4-cyclohexane-diisocyanate, 1-methyl-2,4-cyclohexane diisocyanate, 1-methyl-2,6-cyclohexane diisocyanate and corresponding mixtures of isomers; 4,4'-dicyclohexylmethane diisocyanate, 2,4'-dicyclohexylmethane diisocyanate, 2,2'-dicyclohexylmethane diisocyanate and corresponding mixtures of isomers; aromatic diisocyanates such as toluene 2,4-diisocyanate, mixtures of toluene 2,4-diisocyanate and toluene 2,6-diisocyanate, 4,4'-diphenylmethane diisocyanate, 2,4'-diphenylmethane diisocyanate and 2,2'-diphenylmethane diisocyanate; mixtures of 2,4'-diphenylmethane diisocyanate and 4,4'-diphenylmethane diisocyanate, urethane-modified liquid 4,4'-diphenylmethane diisocyanates and 2,4'-di-phenylmethane diisocyanates, 4,4'-diisocyanato-diphenylethane-(1,2) and 1,5-naphthylene diisocyanate. The diisocyanates which are preferably used are 1,6-hexamethylene diisocyanate, isophorone diisocyanate, dicyclohexylmethane diisocyanate, mixtures of diphenylmethane diisocyanate isomers with a 4,4'-diphenylmethane diisocyanate content of >96% by weight, and particularly 4,4'-diphenylmethane diisocyanate and 1,5-naphthylene diisocyanate. The cited diisocyanates may be used individually or in the form of mixtures with each other. They may also be used together with up to 15 % by weight (calculated based on the total amount of diisocyanate) of a polyisocyanate, for example triphenylmethane 4,4',4"-triisocyanate or polypfienyl-polymethylene polyisocyanates.

The substances which are used as component B) are linear, hydroxyl-terminated polyols with an average molecular weight $M_n$ of 500 to 10,000, preferably 500 to 5000, most preferably 600 to 2000. These often contain small amounts of nonlinear compounds due to the production routes employed. Therefore, they are frequently referred to as "substantially linear polyols". The preferred polyols are polyester-, polyether- or polycarbonate diols, hydroxyl-terminated polybutadienes, hydroxyl-terminated polysiloxanes or mixtures thereof.

Suitable polyether diols can be produced by the reaction of one or more alkylene oxides which contain 2 to 4 carbon atoms in their alkylene radical with a starter molecule which contains two active, bonded hydrogen atoms. Examples of suitable alkylene oxides include: ethylene oxide, 1,2-propylene oxide, epichlorohydrin, 1,2-butylene oxides and 2,3-butylene oxide. Ethylene oxide, propylene oxide and mixtures of 1,2-propylene oxide and ethylene oxide are preferably used. The alkylene oxides can be used individually, alternately in succession or as mixtures. Examples of suitable as starter molecules include: water, amino alcohols such as N-alkyl-diethanolamines e.g. N-methyl-diethanolamine, and diols such as ethylene glycol, 1,3-propylene glycol, 1,4-butanediol and 1,6-hexanediol. Mixtures of starter molecules may also optionally be used. Other suitable polyether diols are polymerisation products of tetrahydrofuran which contain hydroxyl groups. Trifunctional polyethers in proportions of 0 to 30% by weight with respect to the bifunctional polyethers can also be used, but the maximum amount thereof should be such that a thermoplastically processable product is obtained. These substantially linear polyether diols may be used either individually or in the form of mixtures with each other.

Suitable polyester diols can be produced, for example, from dicarboxylic acids comprising 2 to 12 carbon atoms, preferably 4 to 6 carbon atoms, and polyhydric alcohols. Examples of suitable dicarboxylic acids include: aliphatic dicarboxylic acids such as succinic acid, glutaric acid, adipic acid, suberic acid, azelaic acid and sebacic acid, and aromatic dicarboxylic acids such as phthalic acid, isophthalic acid and terephthalic acid. These dicarboxylic acids can be used individually or as a mixture, e.g. in the form of a mixture of succinic, glutaric and adipic acids. It may optionally be advantageous for the production of the polyester diols if, instead of dicarboxylic acids, the corresponding dicarboxylic acid derivatives are used, such as carboxylic acid diesters comprising 1 to 4 carbon atoms in their alcohol radical, carboxylic acid anhydrides or carboxylic acid chlorides. Examples of polyhydric alcohols include glycols comprising 2 to 10, preferably 2 to 6 carbon atoms, such as ethylene glycol, diethylene glycol, 1,4-butanediol, 1,5-pentanediol, 1,6-hexanediol, 1,10-decanediol, 2,2-dimethyl-1,3-propanediol, 1,3-propanediol and dipropylene glycol. Depending on the desired properties, the polyhydric alcohols can be used on their own or optionally in admixture with each other. Substances which are also suitable include esters of carbonic acid with said diols, particularly those comprising 4 to 6 carbon atoms, such as 1,4-butanediol or 1,6-hexanediol, condensation products of hydroxycarboxylic acids e.g. hydroxycaproic acid, and polymerisation products of lactones, for example caprolactones which are optionally substituted. The polyester diols which are preferably used are ethanediol polyadipate, 1,4-butanediol polyadipate, ethanediol-1,4-butanediol polyadipate, 1,6-hexanediol-neopentyl glycol polyadipate, 1,6-hexanediol-1,4-butanediol polyadipate and polycaprolactones. The polyester diols may be used individually or in the form of mixtures with each other.

The substances which are used as chain extension agents C) are diols, diamines or amino alcohols with a molecular weight of 60 to 500. These are preferably aliphatic diols comprising 2 to 14 carbon atoms, such as ethanediol, 1,6-hexanediol, di-ethylene glycol, dipropylene glycol and particularly 1,4-butanediol. Other suitable chain extension agents, however, are diesters of terephthalic acid with glycols which contain 2 to 4 carbon atoms, such as terephthalic acid-bis-ethylene glycol or terephthalic acid-bis-1,4-butanediol for example, hydroxyalkylene ethers of hydroquinone, such as 1,4-di(-hydroxyethyl)-hydroquinone for example, ethoxylated bisphenols, (cyclo)aliphatic diamines such as isophoronediamine, ethylenediamine, 1,2-propylenediamine, 1,3-propylenediamine, N-methylpropylene-1,3-diamine, 1,6-hexamethylenediamine, 1,4-diaminocyclohexane, 1,3-diaminocyclohexane, N,N'-dimethylethylenediamine and 4,4'-dicyclohexyl-methanediamine for example, and aromatic diamines, such as 2,4-diaminotoluene and 2,6-diaminotoluene, 3,5-diethyl-2, 4-diaminotoluene and 3,5-diethyl-2,6-diaminotoluene for example; and primary, mono-, di-, tri- or tetraalkyl-substituted 4,4'-diamino-diphenylmethanes or amino alcohols such as ethanolamine, 1-aminopropanol or 2-aminopropanol. Mixtures of the aforementioned chain extenders can also be used. Smaller amounts of trifunctional crosslinking agents or of crosslinking agents of higher functionality can also be used in addition, e.g. glycerol, trimethyolpropane, pentaerythritol or sorbitol.

Small amounts of customary monofunctional compounds can be used in addition, e.g. as chain terminators or a demoulding agents. Suitable examples include alcohols such as octanol and stearyl alcohol or amines such as butylamine and stearylamine.

A multiplicity of pharmacologically active substances can be used as active ingredients D), for example substances which exhibit an antithrombotic or antibiotic effect. Example of substances which exhibit an antithrombotic effect and which can be used according to the invention include acetylsalicylic acid and alkali and alkaline earth salts thereof, as well as derivatives of dihydropyridine such as N-methyl-2,6-dimethyl-3, 5-di(methoxycarbonyl)-4-(4-trifluoromethylphenyl)-1,4-dihydropyridine (I).

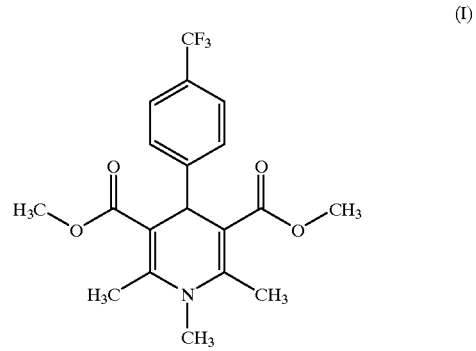

Examples of substances which exhibit an antibiotic effect include ciprofloxacin and fosfomycin. Active ingredients D) are used in amounts of 0.01 to 10% by weight, preferably 0.05 to 7% by weight, most preferably 0.1 to 5% by weight, with respect to the total amount of starting materials. Since the active ingredients are added to the reaction mixture during the production of the TPUs, a homogeneous distribution of these pharmacologically active substances is obtained in the final product without additional operations being required.

Sensitive active ingredients such as heparin are not normally stable at the high temperatures of about 150° C. to 210° C. which are necessary for the thermoplastic processing of polymers. It has surprisingly been shown, however, that active ingredients such as these are stabilised by the method according to the invention, due to their bonding into the polymer matrix, so that they retain their effectiveness even after thermoplastic processing.

The addition of substances having an antithrombotic effect in TPU improves the compatibility with blood of articles produced from this material; the addition of substances having an antibiotic effect acts to prevent the colonisation of germs on the surface. In the course of time, the incorporated active ingredient can in fact partially diffuse to the surface of medical articles, but is not released in therapeutically active concentrations into the surrounding medium, e.g. tissue, blood or other body fluids. If the active substances are decomposed, due to physiological processes, at the interface between the polymer and the surrounding medium, this can be compensated for by the diffusion process. A continuous supply of active ingredient is thereby ensured, so that the desired protection of the surface of the medical article is also ensured over an extended period of time.

The molar ratios of the synthesis components can be varied over a wide range, whereby the properties of the product can be adjusted. Molar ratios of polyols to chain extenders of 1:1 to 1:12 have proved useful. The molar ratio of diisocyanates to polyols is preferably 1.2:1 to 30:1. Ratios of 2:1 to 12:1 are particularly, preferred. For the production of the TPUs, the synthesis components can be reacted, optionally in the presence of catalysts, adjuvant substances and additives, in amounts such that the equivalent ratio of NCO groups to the sum of the groups which are reactive towards NCO, particularly the hydroxy or amino groups of low molecular weight diols/triols, amines and polyols, ranges from 0.9:1 to 1.2:1, preferably from 0.98:1 to 1.05:1, most preferably from 1.005:1 to 1.01:1.

The polyurethanes which can be used in the method according to the invention can be produced without catalysts. In some cases the use of catalysts may be indicated, however. Catalysts are generally used in amounts of up to 100 ppm with respect to the total amount of starting materials. Catalysts which are suitable according to the invention are the customary tertiary amines which are known in the art, such as triethylamine, dimethylcyclohexylamine, N-methylmorpholine, N,N'-dimethyl-piperazine, 2-(dimethylamino-ethoxy)-ethanol, diazabicyclo-(2,2,2)-octane and the like, as well as organometallic compounds in particular such as esters of titanic acid, iron compounds, tin compounds e.g. tin diacetate, tin dioctoate, tin dilaurate or dialkyltin salts of aliphatic carboxylic acids. Dibutyltin diacetate and dibutyltin dilaurate are preferred; amounts of 1 to 10 ppm thereof are generally sufficient to catalyse the reaction.

Apart from the TPU components and catalysts, other additives and adjuvant substances may also be added. Suitable examples include internal lubricants such as fatty acid esters, metal soaps thereof, fatty acid amides, silicone compounds, anti-seizing agents, inhibitors, stabilisers against hydrolysis, light, heat and discoloration, flame retardants, colorants, pigments, and inorganic or organic fillers and reinforcing agents. In particular, the reinforcing agents which are used comprise fibrous reinforcing agents such as inorganic fibres which are produced according to the prior art and which may also be provided with a coating of size. More detailed information on said additives and adjuvant substances is available in the specialist literature, for example J. H. Saunders, K. C. Frisch: "High Polymers", Volume XVI, Polyurethane, Parts 1 and 2, Interscience Publishers 1962 and 1964, respectively; R. Gächter, H. M üller (Eds.): Taschenbuch der Kunststoff-Additive, 3rd Edition, Hanser Verlag, Munich 1989, or DE-A 29 01 774.

The thermoplastically processable polyurethane elastomers are preferably synthesised step-wise by what is termed the prepolymer method. In the prepolymer method, an isocyanate-containing prepolymer is formed from the polyol and the diisocyanate, and this prepolymer is reacted with the chain extender in a second step. The TPUs can be produced continuously or batch-wise. The best-known industrial methods of production are the belt method and the extruder method.

The present invention also relates to the use of the thermoplastic polyurethanes which are treated according to the invention for the production of medical articles, e.g. catheters, flexible tubing, blood bags, films or mouldings for implants.

The TPUs obtained by the method according to the invention can be processed to form mouldings, tubing or films by customary methods such as extrusion or injection moulding. These mouldings are free from pinholes, are flexible, do not stick and can be sterilised without problems by customary methods.

EXAMPLES

Example 1

2880 g (1.373 moles) polytetrahydrofuran with an average molecular weight of 2000 g/mole were placed in a 6 liter flask fitted with a ground glass joint, stirrer, thermometer and reflux condenser and were dried at 120° C./14 mbar for 1 hour. 0.12 g dibutyltin laurate, as a catalyst, and 1528.9 g (5.829 moles) $H_{12}$MDI were then added and the batch was stirred at 120° C. until an NCO value of 8.5% by weight was reached. 48.4 g (1.0% by weight with respect to the total amount of starting materials) calcium acetylsalicylate were first stirred into this prepolymer, followed by 391.1 g (4.341 moles) 1,4-butanediol as a chain extender. After about 60 seconds the reaction mixture was poured on to a coated metal sheet, where it solidified after a few minutes. It was heated for a further 12 hours at 100° C. in order to complete the reaction.

The reacted sheets were cut up and comminuted. The chopped granular material was extruded in a double-shaft Brabender experimental extruder and granulated into lengths. Flexible tubes of inside diameter 3 mm were extruded from the granular material for blood compatibility tests.

Example 2

2880 g (1.373 moles) polytetrahydrofuran with an average molecular weight of 2000 g/mole were placed in a 6 liter flask fitted with a ground glass joint, stirrer, thermometer and reflux condenser and were dried at 120° C./ 14 mbar for 1 hour. 0.12 g dibutyltin laurate, as a catalyst, and 1528.9 g (5.829 moles) $H_{12}$MDI were then added and the batch was stirred at 120° C. until an NCO value of 8.5% by weight was reached. 4.8 g (0.1% by weight with respect to the total amount of starting materials) N-methyl-2,6-dimethyl-3,5-di(methoxycarbonyl)-4-(4-trifluoro-methylphenyl)-1,4-dihydropyridine were first stirred into this prepolymer, followed by 391.1 g (4.341 moles) 1,4-butanediol as a chain extender. After about 60 seconds the reaction mixture was poured on to a coated metal sheet, where it solidified after a few minutes. It was heated for a further 12 hours at 100° C. in order to complete the reaction.

The reacted sheets were cut up and comminuted. The chopped granular material was extruded in a double-shaft Brabender experimental extruder and granulated into lengths. Flexible tubes of inside diameter 3 mm were extruded from the granular material for blood compatibility tests.

Example 3 (Comparative)

2880 g (1.373 moles) polytetrahydrofuran with an average molecular weight of 2000 g/mole were placed in a 6 liter flask fitted with a ground glass joint, stirrer, thermometer and reflux condenser and were dried at 120° C./14 mbar for 1 hour. 0.12 g dibutyltin laurate, as a catalyst, and 1528.9 g (5.829 moles) $H_{12}MDI$ were then added and the batch was stirred at 120° C. until an NCO value of 8.5% by weight was reached. 391.1 g (4.341 moles) 1,4-butanediol were stirred into this prepolymer as a chain extender. After about 60 seconds the reaction mixture was poured on to a coated metal sheet, where it solidified after a few minutes. It was heated for a further 12 hours at 100° C. in order to complete the reaction. The reacted sheets were cut up and comminuted.

Part of the chopped granular material was extruded in a double-shaft Brabender experimental extruder and granulated into lengths. Flexible tubes of inside diameter 3 mm were extruded from the granular material for blood compatibility tests.

Example 4 (Comparative)

In order to produce a master batch, 475.2 g of the chopped granular material from Example 3 were suspended in ethanol and treated with 4.8 g N-methyl-2,6-dimethyl-3, 5-di-(methoxycarbonyl)-4-(4-trifluoromethylphenyl)-1,4-dihydro-pyridine. Thesuspension was freed from ethanol in a rotary evaporator and was dried under vacuum at 40° C. in a drying oven.

The 1% by weight master batch was mixed with 4320 g of chopped granular material which was free from active ingredient and was extruded in a double-shaft Brabender experimental extruder. A clear melt was obtained, which was free from pinholes, and which produced a colourless, clear, non-sticky cylindrical granular material after cooling in a water bath and granulation to form lengths. Flexible tubes of internal diameter 3 mm were extruded from the cylindrical granular material for blood compatibility tests.

Example 5 (Comparative)

In order to produce a master batch, 432 g of the chopped granular material from Example 3 were suspended in ethanol and treated with 48 g calcium acetylsalicylate. The suspension was freed from ethanol in a rotary evaporator and was dried under vacuum at 40° C. in a drying oven.

The 10% by weight master batch was mixed with 4320 g of chopped granular material which was free from active ingredient and was extruded in a double-shaft Brabender experimental extruder. A clear melt was obtained, which was free from pinholes, and which produced a colourless, clear, non-sticky cylindrical granular material after cooling in a water bath and granulation to form lengths. Flexible tubes of internal diameter 3 mm were extruded from the cylindrical granular material for blood compatibility tests.

Dynamic In Vitro Blood Compatibility Tests

In order to characterise the in vitro thrombogenetic effect of the polymer surfaces in contact with blood, freshly taken human blood was treated with citrate or hirudin in order to suppress clotting. After a flexible tube made of the material to be tested had been filled with blood and the tube ends had been joined, the ring of tubing was stretched for a predetermined period over a drum which rotated vertically at a constant speed.

In order to assess the compatibility with blood, various blood clotting factors from different stages of the clotting cascade, blood platelets, and red and white blood corpuscles were determined and assessed according to the following system of points scored: platelet activation 0–5 points, plasmatic clotting 0–30 points, haemolysis 0–10 points, proteolysis 0–10 points. A maximum of 60 points could be obtained; the smaller the number of points obtained, the better was the compatibility with blood. The results of these tests are compared in Table 1.

TABLE 1

| | In vitro compatibility with blood | | | | |
|---|---|---|---|---|---|
| | Example 1 | Example 2 | Example 3* | Example 4* | Example 5* |
| Platelet activation | 3 | 3 | 2 | 3 | 2 |
| Plasmatic clotting | 1 | 2 | 7 | 3 | 3 |
| Haemolysis | 5 | 1 | 4 | 0 | 0 |
| Proteolysis | 1 | 1 | 1 | 0 | 1 |
| Sum | 10 | 7 | 14 | 6 | 6 |

*comparative examples not according to the invention

Example 6 (Comparative)

720 parts by weight polytetrahydrofuran with an average molecular weight of 2000 g/mole and 76.6 parts by weight 1,6-hexanediol were placed in a flask fitted with a ground glass joint, a stirrer and an internal thermometer and were dried for 1 hour at 120° C./14 mbar. 329.8 parts by weigh isophorone diisocyanate were then added and the batch was stirred for 3 hours at 120° C. until an NCO value of 3.5% by weight was reached. 12 parts by weight ethylene-bis-stearylamide and 15.3 parts by weight di-n-butylamine were then added. This prepolymer was dissolved in 634 parts by weight toluene and a solution of 73.6 parts by weight 5-amino-3-aminomethyl-1,3,3-trimethylcyclohexane in 2990 parts by weight of a mixture of toluene and isopropanol in a ratio 70:30 was added drop-wise at room temperature with stirring. A colourless, transparent homogeneous solution was obtained, which resulted in a colourless, transparent, non-sticky film after drying. The latter was chopped and injection moulded to produce test specimens on which bacterial adhesion was measured in suspensions of S. aureus and S. epidermis.

Example 7

A prepolymer which was produced analogously to that of Example 6 was dissolved in 634 parts by weight toluene, and a solution of 73.6 parts by weight 5-amino-3-aminomethyl-1, 3,3-trimethylcyclohexane and 12.4 parts by weight ciprofloxacin in 2990 parts by weight of a mixture of toluene and isopropanol in a ratio 70:30 was added drop-wise at room temperature with stirring. A colourless, transparent homogeneous solution was obtained, which resulted in a colourless, transparent, non-sticky film after drying. The latter was chopped and injection moulded to produce test specimens on which bacterial adhesion was measured in suspensions of S. aureus and S. epidermis. Compared with the sample which was prepared as in Example 6 and which was free from active ingredients, a reduction in bacterial adhesion by more than 99% was determined.

What is claimed is:

1. A method of producing a thermoplastically processable polyurethanes which contain active ingredients by the reaction of the polyurethane-forming components consisting essentially of A) an organic diisocyanate, B) a linear hydroxy-terminated polyol having a molecular weight of 500 to 10,000, and C) chain extenders having a molecular weight of 60 to 500, and adding during the reaction of A), B) and C), D) 0.01 to 10% by weight, with respect to the total amount of starting materials, of a pharmacologically active substance, wherein the molar ratio of the NCO groups in A) to the groups in B) and C) which are reactive towards isocyanate is 0.9 to 1.2 and the molar ratio of B) to C) is 1:1 to 1:12 and the molar ratio of A) to B) is 1.2:1 to 30:1.

2. The method of claim 1 wherein pharmacologically active substance is selected from the group consisting of antithrombotic and antibiotic substances.

3. The method of claim 2 wherein said antithrombotic substance is at least one member selected from the group consisting of acetylsalicylic acid, alkali metal salts of acetylsalicylic acid, alkaline earth metal salts of acetylsalicylic acid and derivatives of dihydropyridine.

4. The method of claim 3 wherein said derivative of dihydropyridine is N-methyl-2, 6-dimethyl-3,5-di(methoxycarbonyl)-4-(4-trifluoromethylphenyl)-1,4-dihydropyridine.

5. The method of claim 2 wherein said antibiotic substance is selected from the group consisting of ciprofloxacin and fosfomycin.

6. The thermoplastically processable polyurethane prepared by the method of claim 1.

7. The thermoplastically processable polyurethane prepared by the method of claim 2.

8. The thermoplastically processable polyurethane prepared by the method of claim 5.

9. Thermoplastically molded articles comprising the polyurethane of claim 6.

* * * * *